United States Patent [19]

Simpson et al.

[11] 4,396,713

[45] Aug. 2, 1983

[54] RESTRICTION ENDONUCLEASE FINGERPRINTING OF KINETOPLAST DNA MINICIRCLES

[75] Inventors: Larry P. Simpson, Los Angeles, Calif.; Carlos M. Morel, Rio de Janeiro, Brazil

[73] Assignee: The Regents of the University of Calif., Berkeley, Calif.

[21] Appl. No.: 206,200

[22] Filed: Nov. 12, 1980

[51] Int. Cl.$^3$ .................... C12Q 1/68; C12Q 1/34; C12Q 1/04; C12P 19/34

[52] U.S. Cl. .................... 435/6; 435/18; 435/34; 435/91; 435/92; 435/803; 435/810

[58] Field of Search .................... 455/46, 34, 89, 90, 455/91, 92, 172, 803, 810, 18; 23/230 B; 424/1, 1.5

[56] References Cited

PUBLICATIONS

Mattei et al., "Biochemical Strain Characterization of *Trypanosoma Cruzi* by Restriction Endonuclease Cleavage of Kinetoplast—DNA" *FEBS. Letters*, vol 74, No. 2 (1977) pp. 264–268.

Borst, et al., "Characterization of DNA from Tyrpanosoma Brucei and Related Trypanosomes by Restriction Endonuclease Digestion", *Chem. Abstracts*, vol 93, No. 21 (1980), p. 221, Nos. 199423p.

Simpson et al., "Replication and Transcription of Kinetoplast DNA", *Chem. Abstracts*, vol. 92, No. 17, (1980), p. 275 Abts. No. 143068p.

Riou, et al., "Heterogeneity of the Kinetoplast DNA molecules of Trypanosoma Cruzi", *Chem. Absts.*, vol. 87, No. 5 (1977) p. 120 Absts. No. 34600g.

Brack, et al., "The use of Restriction Endonucleases for the Investigation of Kinetoplast DNA", *Chem. Absts.* vol. 87, No. 9, (1977), p. 269, Absts. No. 65075u.

Frasch, et al. "The Kinetoplast DNA of Trypanosoma Equiperdum", *Biochim. Biophys., Acta*, vol. 607 (1980), pp. 397–410.

Williams, et al., "Genomic Rearrangements Correluted with Antigenia Variaton in *Trypanosoma Lovercsi*" *Nature* 282 (1979) pp. 847–849.

Mattei, et al. "Biochemical Strain Characterization of *Trypanosoma Cruzi*, by Restriction Endonuclease Cleavage of Kinetoplast DNA", *Chem. Absts.*, vol. 86 No. 19 (1977) p. 267, Abs. No. 136213(e).

Donelson, et al., "Kinetoplast DNA Minicircles of *Trypanosoma Brucei* Share Regions of Sequence Homology," *Chem. Abstracts*, vol. 93 No. 25 (1980) p. 936, Absts. No. 234674v.

*Primary Examiner*—Thomas G. Wiseman
*Attorney, Agent, or Firm*—Bertram I. Rowland

[57] ABSTRACT

Hemoflagellates are characterized by restriction endonuclease digestion of the mitochondrial DNA to provide for substantial cleavage of the kDNA network. The resulting electrophoretic profile of the digest can be used as a restriction fingerprint for distinguishing organisms and specific strains. The kDNA is found to be sufficiently stable through numerous passages of the organism to provide a reliable fingerprint.

11 Claims, No Drawings

RESTRICTION ENDONUCLEASE FINGERPRINTING OF KINETOPLAST DNA MINICIRCLES

The Government has rights to this invention pursuant to Grant No. INT-78-21142 awarded by the National Science Foundation.

BACKGROUND OF THE INVENTION

1. Field of the Invention

Chagas' disease whose etiological agent is the hemoflagellate *Trypanosoma cruzi* is a pleomorphic clinical entity that is an important cause of morbidity and mortality in Central and South America. In some patients the infection is devastating from the very beginning with death following after a short acute phase, where meningoencephalitis and myocarditis are prominent findings. In other cases, however, the acute phase is oligosymptomatic or even inapparent and may evolve without detectable sequels. Between these two extremes, most cases course with a variable acute phase, which subsides in a few weeks, to be followed years later by digestive or cardiac symptoms or both.

The exact causes of this clinical pleomorphism are not known, although evidence from experimental infections of animals suggests that host as well as parasite factors may be involved. Concerning the etiological agent, differences have also been found among several strains of *T. cruzi* as to their morphology, virulence, pathogenicity, tropism and other parameters. Particularly well documented and studied are the differences between the Y and CL strains of *T. cruzi*. These strains, termed "polar" by Brener (1977) Pan American Scientific Organization, Scientific Publication 347:11–21, differ significantly according to various parameters which include growth in culture medium and in tissue culture, as well as in morphology and in tissue tropism.

The above mentioned differences among *T. cruzi* strains and recent reports support the belief that *T. cruzi* is not a homogeneous species. It is therefore important to be able to identify *T. cruzi* subgroups and relate them to observed pathology. Not only is this of interest with *T. cruzi*, but other organisms of the order Kinetoplastida, which share a common characteristic in the nature of their mitochondrial DNA. The mitochrondrial DNA is composed of a multiplicity of catenated, covalently closed minicircles and maxicircles organized into a two-dimensional network. This unique form of DNA offers the potential to use the electrophoretic distribution of an endonuclease digest as a diagnostic characteristic of a particular species or strain.

2. Description of the Prior Art

The minicircle component of the kDNA network of hemoflagellate protozoa consists of a few to many semihomologous sequence classes that all appear to share a constant region. Donelson et al. (1979) Plasmid 2:572–588; Steinert and Van Assel, (1980) Plasmid 3:7–17. kDNA from different hemoflagellate species have few, if any, sequences in common and kDNAs from different strains of *Leishmania*, or Trypanosoma vary by hybridization of cRNA and even by buoyant density analysis. Chance (1977) In: "Biochemistry of Parasites and Host Parasite Relationship." (Van den Bossche, H. ed.), Elsevier, Amsterdam, pp. 229–235; Steinert, et al. (1976) In: "The Genetic Function of Mitochondrial DNA." (Sacone and Kroon, eds.), Elsevier, Amsterdam, pp. 71–81; Newton & Burnett (1972) In: Comparative Biochemistry of Parasites. (Van den Bossche, H. ed.), Academic Press, N.Y. pp. 127–138. Classification of different strains and species of Leishmania and *T. cruzi* by means of kDNA buoyant analysis has been performed by Chance and Baker et al. Chance (1979) In: "Problems in the identification of parasites and their vectors." (Taylor and Muller, eds.) Blackwell Science Pub., Oxford, pp. 55–74; Baker et al., (1978) Am. J. Trop. Med. Hyg. 27:483–491. Mattei et al., (1977) FEBS Letters 74:264–268, report that different *T. cruzi* strains gave different kDNA restriction fingerprints in 3.5% acrylamide gels. Brack et al., (1976) In: Biochemistry of Parasites and Host-Parasite Relationships, (Van den Bossche, H., ed.), Elsevier/North Holland Biomedical Press, Amsterdam, pp. 211–218, also demonstrates the validity of species classification by restriction profiles of kDNA. Riou & Gutteridge, (1978) Biochimie 60:365–379 report the lack of qualitative differences between dDNA restriction profiles of two *T. cruzi* strains, while Leon et al., (1977) In: Congresso Internacional sobre Doenca de Chagas, Proceedings of an International Symposium, Fundacao Oswaldo Cruz, Rio de Janeiro, Brazil, page 77, and Leonet al., (1980) Biochim. Biophys. Acta 607:221–231, report extensive differences in kDNA restriction profiles between two isolates of the Y strain of *T. cruzi* and published profiles of Y strain kDNA, and conclude that minicircle digestion patterns might not be a stable and reliable criterion for strain characterization.

SUMMARY OF THE INVENTION

Method is provided for diagnosing kinetoplastida strains involving restriction endonuclease digestion of mitochondrial kDNA with enzymes providing for significant degradation of the minicircles. The resulting digest is separated into fragments by high resolution acrylamide gradient gel electrophoresis to provide a gel profile. The resulting profile can be used as diagnostic of the Kinetoplastida strain. In combination with other techniques such as buoyant density and isozyme analysis, the subject method provides for an accurate classification of parasitic hemoflagellates.

DESCRIPTION OF THE SPECIFIC EMBODIMENTS

In accordance with the subject invention, parasitic hemoflagellates can be rapidly assayed and classified as to subgenus and strain. The method depends upon the relative compositional and sequence stability of mitochondrial kDNA as diagnostic of a particular hemoflagellate strain. Strains of particular interest are those of the *Trypanosoma cruzi*, *Trypanosoma brucei*, and *Leishmania sp.* as illustrative of specific species.

The method involves three stages. Isolation of kDNA from a cell culture, desirably a clone; restriction endonuclease digestion of the isolated kDNA; and high resolution gel electrophoresis.

The first stage involves isolation of the kDNA. The sample to be assayed is obtained from blood with the cells grown to stationary phase in an appropriate medium, for example liver infusion-tryptose medium (LIT) (Mattei et al, supra). When cloning is employed, the cloning can be performed on 1% LIT-agar by streaking a cell suspension and isolating single colonies.

After suspending the cells in a buffered saline medium, having from about 0.05 to 0.25 M NaCl and from about 0.05 to about 0.5 M EDTA, with a pH of about 7.5 to 8.5, preferably 8.0 with a maximum density not to exceed about $1.2 \times 10^9$ cells per ml, the cells are enzymatically lysed in accordance with known techniques. To reduce viscosity and facilitate recovery of the kDNA, the lysates may be subjected to mild shearing. The network DNA is then pelleted by centrifugation and may be further purified by resuspension in an appropriate buffered medium and recentrifugation. After resuspension in an appropriately buffered medium, desirably about 5 to 20 mM Tris and about 0.5 to 2 mM EDTA, pH 7.5 to 8.5, the aqueous suspension is extracted with organic solvents, particularly initially with a phenol/chloroform mixture saturated with aqueous saline Tris of about 25 to 75 mM, pH 7 to 8, followed by ether extraction, ethanol precipitation, and resuspension in Tris buffer.

The kDNA preparation is then digested in appropriate buffers to substantially complete, preferably complete digestion. The choice of restriction endonuclease will depend upon the particular Kinetoplastida strain. Desirably, at least about 20% of the minicircles of the kDNA should be cleaved at least twice, preferably at least about 35%. As appropriate, endonuclease digestion may involve two or more restriction enzymes, generally not involving more than four, preferably not more than about three. Preferably, a single or two enzymes will provide for the desired degree of digestion.

Illustrative restriction enzymes include:

Table 1

1. EcoRI, HaeIII, HinfI, MspI, TaqI
2. AluI, AVAII, FnuDII, HhaI, KpnI, MboI
3. AluI, BglII, BstEII, HincII, HpaI, XbaI.

With the Y and CL strains of *T. cruzi*, the best results were obtained with Group 1, with diminishing amounts of digestion occurring with Groups 2 and 3. TaqI was found to cleave most of the minicircles more than once. Depending upon the degree of complexity desired in the electrophoresis profile for providing the strain fingerprint, one or a plurality of enzymes may be employed.

The conditions employed with the restriction endonucleases are conventional and may vary from enzyme to enzyme. The enzyme concentration, and the time and temperature employed should allow for complete digestion of the available restriction sites of the kDNA.

After complete digestion of the kDNA, the kDNA may be combined with an appropriate dye, or initially precipitated and resuspened in an appropriate dye solution. The kDNA solution is then loaded directly onto the gel, generally having about 3% polyacrylamide and desirably having a polyacrylamide linear gradient varying from about 3.5 to 10% with the 3% polyacrylamide as the top layer. After electrophoresis, in accordance with conventional techniques, the gel may be stained to determine the band distribution.

By appropriate employment of standards, one can develop an intrinsic characterization of stocks (population derived by serial passage in vivo and/or in vitro from a primary isolation, without any implication of homogenity or characterization), strains (a set of populations originating from a group of microorganisms of a given species or subspecies present at a given time in a given host or culture and defined by the possession of one or more designating characters) and clones (microorganisms derived from a single individual by binary fision) and use this characterization for comparison to unknown pathogenic hemoflagellates for a determination of the particular strain. By diagnosing the particular strain, one may relate this to the known pathogenicity of the strain and use the diagnosis for treatment.

In addition, strains may be further classified as zymodeme groups and schizodeme groups. for *T. cruzi* trypanosomes, differences in enzyme patterns have resulted in groupings of four zymodemes, A–D. Based on differences in kDNA minicircle restriction profiles trypanosomes can be subdivided into schizodeme subpopulations, where members of a schizodeme have substantially the same restriction profile.

The following examples are offered by way of illustration and not by way of limitation.

EXPERIMENTAL

With the exception of the "polar" strains Y and CL, Brener, supra, all the *T. cruzi* stocks used were obtained from patients with reactive serology against Chagas' disease. Stock cultures were initiated with cells from 30 ml of blood grown to stationary phase in liver infusion-tryptose medium (LIT) (Canargo (1964) Rev. Inst. Med. Trop. Sao Paulo 6:93–100) at 27° C. and frozen in liquid nitrogen. The stocks were numbered consecutively. For kDNA isolation, 30–60 ml cultures were initiated from frozen stabilates and the cells washed in Krebs-Ringer-Tris buffer and stored as pellets at −70° C. until processing. Y and CL cells were grown in LIT medium and stored at −70° until processing, unless indicated otherwise.

Isozyme patterns were determined as described by Romanha et al. (1979) Comp. Biochem. Physiol. 62B:139–142 and Romanha et al. (1979) In: Congresso Internacional sobre Doenca de Chagas. Proceedings of an International Symposium, Rio de Janeiro, Brazil, 22–28, July 1979. Fundacao Oswaldo Cruz, Rio de Janeiro, RJ, Brazil, page 70. The electrophoretic patterns of the following soluble enzymes were used: alanine amino-transferase, glucose-phosphate isomerase, glucose-6-phosphate dehydrogenase, phosphoglucomutase, 6-phosphogluconate dehydrogenase, malic enzyme, aspartate aminotransferase and malate dehydrogenase.

For the preparation of kDNA, a modification of the method described in Simpson & Berliner, (1974) J. Protozool. 21:382–383 for *L. tarentolae* was used. *T. cruzi* cells were suspended in 0.15 M NaCl, 0.1 M EDTA, pH 7.9 (SE) at a maximum density of $1.2 \times 10^9$ cells/ml. Pronase$^{CB}$(10 mg/ml in SE, predigested at 37° C. for 30 min) was added to 0.5 mg/ml and sarkosinate (30% stock solution) to 3% and the lysate was incubated at 60° C. for 3 hr. In order to reduce the viscosity and facilitate recovery of network DNA, lysates were diluted with SE and sheared through a #18 needle at about 12–25 psi or by hand with a syringe. Network DNA was pelleted either in the SW27 rotor (27,000 rpm, 1 hr), in the Sorvall HB-4 rotor (9,000 rpm, 2 hr) or in an Eppendorf Microfuge (13,000×g, 1 hr) at 5° C. The pellets were then resuspended in the original volume in 10 mM Tris HCl-1 mM EDTA, pH 7.9 (TE) by shaking at 37° C., and were centrifuged as above. The pellets were then resuspended in TE (400 µl for up to $1.2 \times 10^{10}$ cells) and extracted twice with phenol/chloroform (1:1, V:V, saturated with 50 mM Tris HCl-0.1 M NaCl, pH 7.4) and four times with ether, followed by ethanol precipitation, drying and resuspension in TE at 100 µl/$10^9$ cells.

The kDNA preparations were digested with aliquots of 5–10 µl of the kDNA preparation in an appropriate buffer in a final volume of 50 μl with an excess of enzyme. After 1.5 hrs. of digestion at 37° C. (60° C. for TaqI), the DNA was ethanol-precipitated, dried and resuspended in 10 μl of 25% glycerol, 2.5% sodium sarkosinate, 0.025% bromphenol blue, 0.025% xylene cyanol CFF. In some cases the reactions were performed in 20 μl volumes and loaded directly on gels after the addition of glycerol-sarkosyl-dye solution.

Electrophoresis was performed in 3.0% +3.5–10% acrylamide linear gradient gels as described by Simpson (1979) Proc. Nat. Acad. Sci. USA 76:1585–1588 or, when Southern transfers were required, in 2% agarose gels. (Southern (1975) J. Mol. Biol. 98:503–517) As a reference DNA, a mixture of phage lambda DNA digested with HindIII and phage φX174 RF digested with HaeIII was used. After staining with 1.0 μg/ml ethidium bromide for 30 mins the gels were transilluminated with a 300 nm ultraviolet source and photographed on Kodak Royal Pan or Tri-X film (Brunk and Simpson (1977) Anal. Biochem. 82:455–462).

The labeling of kDNA and hybridization was achieved by labeling the kDNA by nick translation using $\alpha\text{-}^{32}\text{P-dCTP}$ as described by Rigby et al. (1977) J. Mol. Biol. 113:237–251. Transfer of DNA fragments from agarose gels to aminophenylthioether paper and hybridization with the labeled probe was performed according to Masuda et al. (1977) Gene 6:51–73.

In accordance with the above described protocol, minor nuclear DNA contamination does not interfere and the yield of kDNA is high. Cells from a standard 30 ml culture of $T.$ $cruzi$ in LIT at a density of $45\text{-}70 \times 10^6$ cells/ml yield enough DNA for more than 25 electrophoretic runs. Based on tests with the kDNA from Y and CL "polar" strains, six enzymes AluI, AvaII, FnuDII, HhaI, KpnI and MboI besides releasing linearized minicircles also produce smaller fragments from at least one of the strains tested, while five enzymes: EcoRI, HaeIII, HinfI, MspI and TaqI, gave the best fingerprints for comparative purposes, with a high percentage of fragments smaller than minicircle size. TaqI was unique in that it cleaved most of the minicircles more than once giving rise to complex patterns in which a band with one-fourth the molecular weight of the minicircle predominates.

Comparison of EcoRI and HinfI digests of the kDNA from the Y and CL strains and the kDNA from stocks 269, 271, 231 and 280, which represent randomly selected representatives of zymodeme groups A, B, C and D, show quantitative as well as qualitative differences between the restriction profiles, with the exception of the digests of strain CL and stock 271, which were identical with all restriction enzymes tested.

Evidence that similarities in restriction profiles represent similarities in DNA sequences was obtained by a Southern blot hybridization experiment. kDNA from the six strains was digested with EcoRI and the fragments separated in agarose. The gel was blotted and the blot was hybridized with nick translated $\alpha\text{-}^{32}\text{P}$-labeled CL kDNA probe. The results show that the CL probe lit up the 271 kDNA to the same extent as the homologous CL kDNA and also lit up the 231 kDNA to a lesser extent. The Y, 269 and 280 kDNAs showed little hybridization.

kDNA from strain CL was digested with EcoRI, Hae III, TaqI and every possible combination of these enzymes. The single enzyme digests share major bands, particularly in the case of EcoRI and HaeIII. The EcoRI/HaeIII double digest represents the sum of patterns of the individual digests, suggesting a close clustering of the sites for these enzymes in the minicircles. Double and triple digestions which included TaqI gave rise to new low molecular weight bands as expected for distantly located sites.

The usefulness of kDNA minicircle restriction profiles as intrinsic parameters of strain classification was established by demonstrating genetic stability of minicircle sequences. Six randomly selected $T.$ $cruzi$ stocks belonging to zymodeme group C were analyzed. Each stock was isolated from a different human case of Chagas' disease. Although the patients differed in many parameters such as sex, age, date of infection and genetic constitution and although the samples for the hemoculture were collected and processed at different times, the six EcoRI and HinfI restriction patterns were clearly very similar when not identical. Similar results were obtained with MspI and BspRI digests. These were also similar to the profile of stock 231 which was prepared and analysed at a different place and time. These results, together with the similarity of profiles of strain CL kDNA (isolated from an insect vector in South Brazil) and stock 271 kDNA (isolated from a patient in Southeast Brazil) point to a rather good genetic stability of kDNA minicircle restriction fingerprints.

Another qualitative estimate of the range of change of $T.$ $cruzi$ kDNA minicircle sequences was obtained by comparisons of kDNA from CL cultures kept at $-70°$ C. for two years with kDNA from the same cells after two years in continuous culture or after two years in mice. No differences in the kDNA minicircle restriction profiles were apparent after the two year period of serial culture, but a few minor changes were detected after two years serial passage in the mouse host. No change in the minicircle restriction patterns was found with growth conditions, such as log phase vs. stationary phase. Furthermore, the proportion of trypomastigotes in the culture had no effect on the kDNA restriction profile. From this it is concluded that the $T.$ $cruzi$ kDNA minicircle sequences change rapidly enough in nature to produce differences between different strains, but not so rapidly as to preclude a laboratory analysis after establishment of a stock hemoculture.

In accordance with the subject invention, a simple, efficient and rapid method is provided for analyzing strains of Kinetoplastida. It is found that strains of Kinetoplastida retain the genetic integrity of minicircles for sufficiently long periods of time to allow for restriction endonuclease digestion to be diagnostic of the particular strain. By employing high resolution electrophoresis, unique profiles can be obtained so that the observed bands of the clinical isolate can be compared to standards obtained from other sources. The reagents employed for the assay can be standardized and provided as kits. In addition, profiles can be established as prints of the bands, so as to provide a comparison library which is convenient and readily accessible.

Although the foregoing invention has been described in some detail by way of illustration and example for purposes of clarity of understanding, it will be obvious that certain changes and modifications may be practiced within the scope of the appended claims.

What is claimed is:

1. A method for assaying for the presence in a sample of a stock or strain within a species of hemoflagellate which comprises:

isolating kDNA from a cell culture from said sample;

restriction endonuclease digesting said isolated kDNA with at least one restriction endonuclease selected from the group consisting of EcoRI, HaeIII, HinfI, MspI, and TaqI to provide for cleavage of minicircles present in said kDNA, wherein at least 20% of the minicircles are cleaved at least twice;

electrophoresing the digested kDNA under conditions of high resolution to provide a schizodeme profile unique to a particular hemoflagellate strain or stock; and comparing said profile with a known hemoflagellate strain or stock digested and electrophoresed in substantially the same manner as said kDNA from said sample cell culture to determine the presence of said known hemoflagellate in said sample.

2. A method according to claim 1, wherein said high resolution employs a linear gradient polyacrylamide gel.

3. A method according to claims 1 or 2, where one of said restriction enzymes is TaqI.

4. A method according to claims 1, or 2, where one of said enzymes is EcoRI.

5. A method according to claim 1, where said hemoflagellate is a trypanosome.

6. A method for assaying for the presence in a sample of a Kinetoplastida strain, which comprises:

growing microorganisms in a nutrient medium from a sample suspected of containing Kinetoplastida;

lysing the cells and isolating the cells by means of centrifugation to provide a pellet;

suspending the pellet in an aqueous buffered medium and extracting said medium with at least one organic solvent;

digesting the kDNA with at least one restriction endonuclease selected from the group consisting of EcoRI, HaeIII, HinfI, MspI, and TaqI to cleave at least a substantial proportion of the minicircles present in said kDNA and at least 20% of said minicircles twice;

electrophoresing said digested kDNA under high resolution conditions to provide a profile characteristic of a particular Kinetoplastida strain; and comparing said profile with a known hemoflagellate strain or stock digested and electrophoresed in substantially the same manner as said kDNA from said sample cell culture to determine the presence of said known hemoflagellate in said sample.

7. A method according to claim 6, wherein said Kinetoplastida is a Trypanosoma.

8. A method according to claim 6, wherein said Kinetoplastida is Leishmania.

9. A method according to claims 6, 7 or 8, wherein said digestion employs TaqI.

10. A method according to claim 9, wherein said electrophoresing employs a linear gradient polyacrylamide gel.

11. A method according to claim 10, wherein said lysing is achieved with pronase in the presence of sarkosinate.

* * * * *